United States Patent [19]

Decker et al.

[11] Patent Number: 4,745,228
[45] Date of Patent: May 17, 1988

[54] PREPARATION OF CYCLIC KETONES

[75] Inventors: Martin Decker, Ludwigshafen; Rolf Fischer, Heidelberg; Wolfgang Franzischka; Rudolf Kummer, both of Frankenthal; Heinz-Walter Schneider, Ludwigshafen; Uwe Vagt, Speyer, all of Fed. Rep. of Germany

[73] Assignee: BASF Aktiengesellschaft, Ludwigshafen, Fed. Rep. of Germany

[21] Appl. No.: 65,959

[22] Filed: Jun. 24, 1987

[30] Foreign Application Priority Data

Jul. 1, 1986 [DE] Fed. Rep. of Germany ....... 3622012

[51] Int. Cl.$^4$ .................. C07C 45/00; C07C 45/51
[52] U.S. Cl. .................................................. 568/443
[58] Field of Search ........................................ 568/443

[56] References Cited

U.S. PATENT DOCUMENTS 3,890,370 6/1975 Buchi et al. ...................... 568/443
4,275,238 6/1981 Petree et al. ...................... 568/443

OTHER PUBLICATIONS

Houben-Weyl, Methoden der organischen Chemie, vol. VII/2a, part 1, pp. 637–639, (1973).
Houben-Weyl, Methoden der organischen Chemie, vol. VIII, p. 574, (1952).

Primary Examiner—Werren B. Lone
Attorney, Agent, or Firm—John H. Shurtleff

[57] ABSTRACT

Cyclic ketones of the formula

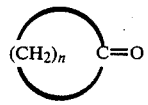

I where n is an integer from 4 to 6, are prepared by converting an aliphatic dicarboxylate of the formula

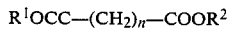

R$^1$OCC—(CH$_2$)$_n$—COOR$^2$  II where n has the above meaning, R$^1$ and R$^2$ are each alkyl, cycloalkyl, aralkyl or aryl and R$^2$ may furthermore be hydrogen, at from 150° to 450° C. over a solid oxide catalyst.

8 Claims, No Drawings

PREPARATION OF CYCLIC KETONES

The present invention relates to a process for the preparation of cyclic ketones by converting an aliphatic dicarboxylate over a solid oxide catalyst in the gas or liquid phase.

It is known that cyclopentanone can be prepared by heating adipic acid in the presence of a catalytic amount of heavy metal salt in the liquid phase. Metals used for this purpose are, for example, barium and thorium (see, for example: Houben-Weyl, Methoden der organischen Chemie, volume VII/2a, part 1, pages 637–639 (1973)). This method has the disadvantage that corrosion problems occur at the high temperatures required and heavy metals are necessary.

It is an object of the present invention to provide an economically attractive and technically simple process for the preparation of cyclic ketones, such as cyclopentanone.

We have found that this object is achieved by a novel process for the preparation of cyclic ketones of the formula

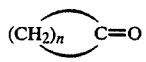   I where n is an integer from 4 to 6, wherein an aliphatic dicarboxylate of the formula

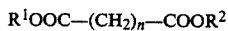   II where n has the above meaning and $R^1$ and $R^2$ are each alkyl of 1 to 12 carbon atoms, cycloalkyl of 5 or 6 carbon atoms, aralkyl or aryl and $R^2$ may furthermore be hydrogen, is converted at from 150° to 450° C. over a solid oxide catalyst.

The reaction according to the invention can be represented, for example for the conversion of dimethyl adipate to cyclopentanone, by the following equation:

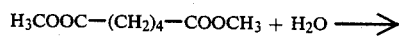

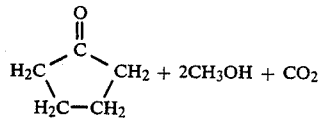

It is known that adipates can be converted to cyclopentanone with the aid of stoichiometric amounts of strong bases, such as sodium alcoholates or sodium amides, via the intermediate cyclopentanone-2-carboxylate in two stages (Dieckmann condensation, cf. Houben-Weyl, Methoden der organischen Chemie, volume VIII, page 574 (1952)). This process requires three steps (condensation, neutralization and hydrolysis and decarboxylation). Moreover, the base used has to be neutralized, so that a substantial amount of neutral salts inevitably results. On the other hand, it is surprising that cyclic ketones, such as cyclopentanone, are obtained in a single stage and furthermore in high yields in the novel process.

The esters of the formula II which are required as starting materials are aliphatic, cycloaliphatic, araliphatic or aromatic mono- or diesters of the relevant dicarboxylic acids, such as adipic acid, pimelic acid or suberic acid. Examples of radicals $R^1$ and $R^2$ are methyl, ethyl, propyl, isopropyl, butyl, isobutyl, tert-butyl, hexyl, nonyl, dodecyl, cyclopentyl, cyclohexyl, phenyl and benzyl.

For example, the following esters can be used as starting materials: dimethyl adipate, monomethyl adipate, diethyl adipate, dibutyl adipate, dicyclohexyl adipate, dibenzyl adipate, dimethyl 1,7-heptanedioate, diethyl 1,7-heptanedioate, monomethyl 1,7-heptanedioate, dibutyl 1,7-heptanedioate, dicyclohexyl 1,7-heptanedioate, dibenzyl 1,7-heptanedioate, dimethyl 1,8-octanedioate, diethyl 1,8-octanedioate, monomethyl 1,8-octanedioate, dibutyl 1,8-octanedioate, dicyclohexyl 1,8-octanedioate and dibenzyl 1,8-octanedioate.

The catalysts used are solid oxide catalysts, for example oxides of elements of main groups I to V and of subgroups I to VIII of the periodic table of elements, or oxides of the rare earth metals or mixtures of the stated oxides. For example, alkaline earth metal oxides, such as magnesium oxide, calcium oxide and barium oxide, boron trioxide, alumina, silica, for example in the form of silica gel, kieselguhr or quartz, tin dioxide, bismuth oxide, copper oxide, zinc oxide, lanthanum oxide, titanium dioxide, zirconium dioxide, vanadium oxides, chromium oxides, molybdenum oxides, tungsten oxides, manganese oxides, iron oxides, cerium oxides, neodymium oxides and mixtures of such oxides are suitable. The catalysts may futhermore be modified by applying additives, such as acids (eg. phosphoric acid) or bases (eg. sodium hydroxide). Magnesium oxide, boron trioxide, alumina, silica, zinc oxide, titanium dioxide and mixtures of these are preferred, alumina catalysts being very particularly suitable.

Although it is possible to carry out the reaction according to the invention without the addition of water, the addition of water results in a remarkable increase in selectivity and catalyst life. The molar ratio of ester II to water is advantageously from 1:0.05 to 1:20, in particular from 1:0.1 to 1:5.

The reaction can be carried out in the gas phase or in the liquid phase, in the presence or absence of diluents. Examples of suitable diluents are solvents which are completely or substantially inert under the reaction conditions, eg. ethers, such as dioxane or tetrahydrofuran. The reaction is preferably carried out in the gas phase, provided that the starting materials are readily vaporizable.

The reaction may be carried out batchwise or continuously using a fixed bed catalyst, for example by the flooded-bed or trickle-bed method in the liquid or gas phase, or as a fluidized-bed reaction with catalysts fluidized upward and downward in the gas phase, or with a fixed bed catalyst suspended in the liquid phase.

The reaction is carried out from 150° to 450° C., preferably from 200° to 400° C., in particular from 300° to 345° C., in general under atmospheric pressure. However, it is also possible to use slightly reduced or slightly superatmospheric pressure, for example up to 20 bar. The space velocity is in general from 0.01 to 40, preferably from 0.1 to 20, g of ester II per g of catalyst per hour.

The reaction in the liquid phase is carried out, for example, as follows: a mixture of the ester and, if required, water is heated to the desired reaction temperature in the presence of a suspended fixed-bed catalyst. After the required reaction time has elapsed, the reaction mixture is cooled and the catalyst is removed, for example by filtration. The reaction mixture is then subjected to fractional distillation to obtain the ketone and the unconverted ester.

In the preferred embodiment of the novel process in the gas phase, for example, a mixture of the ester and water is first vaporized and then, with or without an inert gas, such as nitrogen, carbon dioxide or argon, is passed in gaseous form, at the desired reaction temperature, into a catalyst bed in upward and downward fluidized motion. The reacted mixture is condensed by means of suitable cooling apparatuses and then worked up by fractional distillation. Unconverted ester can be recycled.

The novel process for the preparation of the cyclic ketones, such as cyclopentanone, has the advantage over the known processes that the product is obtained from the readily obtainable esters in one reaction step and in high yield and selectivity.

The cyclic ketones obtainable by the novel process are useful intermediates. For example, cyclopentanone can be subjected to reductive amination to give cyclopentylamine, which is useful for the synthesis of crop protection agents and drugs.

EXAMPLE 1

10 ml/hour of dimethyl adipate (DMA) were pumped into an evaporator and were fed from there, in the form of a gas and together with 3 l of nitrogen, over 15 ml of the catalyst stated in Table 1, at from 300° to 450° C. The gaseous reacted mixtures were condensed in cold traps, weighed, and analyzed by gas chromatography. Table I shows the composition of the reacted mixtures as a function of temperature after an experimental time of 4 hours in each case.

TABLE 1

| No. | Catalyst | Temperature [°C.] | Cyclopentanone [mol %] | DMA [mol %] |
|---|---|---|---|---|
| 1 | 10 g of γ-alumina | 320 | 48 | 38 |
| 2 | 10 g of γ-alumina | 400 | 63 | 6 |
| 3 | 10 g of γ-alumina + 5% of phosphoric acid | 350 | 45 | 39 |
| 4 | 10 g of silica | 450 | 26 | 57 |
| 5 | 26 g of zinc oxide | 350 | 26 | 50 |
| 6 | 23 g of titanium dioxide | 400 | 27 | 43 |

EXAMPLE 2

13 ml/hour of a mixture of 78.5% by weight of DMA, 13.5% by weight of methanol and 8% by weight of water (molar ratio of DMA to $H_2O=1:1$) were pumped into an evaporator and were fed from there, together with 3 l of nitrogen, over 15 ml of catalyst at from 300° to 450° C. The gaseous reacted mixtures were condensed in cold traps, weighed, and analyzed by gas chromatography. Table II shows the catalysts used and the composition of the reacted mixtures.

TABLE 2

| No. | Catalyst | Temperature [°C.] | Cyclopentanone [mol %] | DMA [mol %] |
|---|---|---|---|---|
| 1 | 10 g of γ-alumina | 340 | 74 | 16 |
| 2 | 10 g of γ-alumina | 350 | 69 | 7 |
| 3 | 23 g of titanium dioxide | 400 | 60 | 19 |
| 4 | 10 g of magnesium oxide | 400 | 58 | 8 |
| 5 | 10 g of cobalt oxide (20%) on silica gel | 350 | 70 | 8 |
| 6 | 10 g of lead oxide (75%)/ magnesium oxide (25%) | 400 | 43 | 49 |
| 7 | 10 g of lithium oxide (13.5%)/magnesium oxide | 400 | 62 | 32 |
| 8 | 10 g of tin oxide (20%) on magnesium oxide | 350 | 43 | 42 |
| 9 | 10 g of cesium oxide (13.5%) on silica gel | 350 | 60 | 11 |

EXAMPLE 3

100 ml/hour of DMA were vaporized at 300° C. and passed, together with 30 l of nitrogen, over 200 g (300 ml) of γ-alumina (4 mm extrudates) at 320° C. The gaseous reacted mixture was condensed in cold traps for 7.5 h (total DMA feed: 805 g; total amount of mixture discharged: 569 g; composition of the reacted mixture according to quantitative GC analysis: 32% by weight of cyclopentanone and 52% by weight of DMA) and then subjected to fractional distillation.

162 g (42% of theory) of pure cyclopentanone of boiling point 129°–131° C. were isolated in this manner. In addition, 297 g (37% of theory) of unconverted DMA of boiling point 73°–85° C./2 mbar were recovered.

EXAMPLE 4

10 ml/hour of monomethyl adipate (bp. 162° C./10 mbar) were pumped into an evaporator and fed from there, in gaseous form and together with 3 l of nitrogen, over 10 g (15 ml) of γ-alumina (4 mm extrudates) at 320° C. The gaseous reacted mixture was condensed in cold traps for 10 h, weighed, and analyzed by gas chromatography. The total amount of monoester fed in was 109 g, the total amount of mixture discharged 79 g, the composition of the discharged mixture 42% by weight of cyclopentanone (corresponding to a yield of 58% of theory), 30% by weight of DMA and 4% by weight of the monoester.

EXAMPLE 5

13 ml/hour of a mixture of 78.5% by weight of DMA, 13.5% by weight of methanol and 8% by weight of water (molar ratio of DMA to $H_2O=1:1$) were pumped into an evaporator and fed from there, together with 3 l of nitrogen, over 10 g (15 ml) of γ-alumina (4 mm extrudates) in four test series at 300°, 320°, 330° and 340° C. The gaseous reacted mixtures were condensed in cold traps, weighed, and analyzed by gas chromatography. After the end of the experiment, the reacted mixtures from each of the individual test series were combined, and analyzed by gas chromatography. Table III summarizes the results.

TABLE III

| Test No. | Temperature [°C.] | Test time [h] | DMA feed [g] | Amount discharged [g] | Cyclopentanone [mol %] | DMA [mol %] | Conversion [%] | Selectivity [%] |
|---|---|---|---|---|---|---|---|---|
| 1 | 300 | 168 | 1778 | 1963 | 24 | 66 | 34 | 71 |
| 2 | 320 | 216 | 2366 | 2533 | 30 | 59 | 41 | 73 |
| 3 | 330 | 192 | 1805 | 1571 | 60 | 29 | 71 | 85 |
| 4 | 340 | 72 | 642 | 464 | 49 | 11 | 89 | 55 |

The reacted mixture from test No. 2 (320° C.) was worked up as follows: the low boiling components (cyclopentanone, methanol and water) were first stripped off under reduced pressure. NaCl was added, after which the aqueous phase was separated off and the organic phase subjected to fractional distillation under atmospheric pressure. 211 g (19% of theory) of cyclopentanone were obtained after distillation.

The reacted mixture from test No. 3 (330° C.) was worked up as follows: first, the low boiling components (cyclopentanone, methanol and water) were stripped off under reduced pressure, and dichloromethane was added. The organic phase was separated off and the aqueous phase was washed three times with a little dichloromethane. Combined organic phases were substantially dried by separating off the water together with dichloromethane, and then subjected to fractional distillation under atmospheric pressure. 470 g (54% of theory) of cyclopentanone were obtained after distillation.

EXAMPLE 6

150 ml/hour of DMA and 33 ml/hour of water (molar ratio of DMA to H$_2$O=1:2) were vaporized at about 300° C. and passed, together with 30 l of nitrogen, over 200 g (300 ml) of γ-alumina (4 mm extrudates, catalyst from Experiment 6) at 320° C. The gaseous reacted mixture was condensed in cold traps for 8 hours. The total amount of DMA fed in was 1208 g, the total amount of mixture discharged was 1069 g, and the composition of the discharge mixture according to quantitative GC analysis was 31% by weight of cyclopentanone and 26.5% by weight of DMA.

To work up the mixture, the low boiling components of the reacted mixture (cyclopentanone, water and low boilers such as dimethyl ether and methanol) were stripped off under reduced pressure, and dichloromethane was added. The organic phase was separated off and the aqueous phase was washed three times with a little dichloromethane. The combined organic phases were substantially dried by separating off the water together with dichloromethane and then subjected to fractional distillation under atmospheric pressure. 300 g (51% of theory) of cyclopentanone were obtained after distillation.

EXAMPLE 7

150 ml/hour of DMA and 33 ml/hour of water (molar ratio of DMA to H$_2$O=1:2) were vaporized at about 300° C. and fed, together with 60 l of nitrogen, over 300 g (380 ml) of fluidized γ-alumina catalyst (particle size 0.14–0.315 mm) at 330°–360° C. The gaseous reacted mixture was in each case condensed in cold traps and analyzed by gas chromatography. The results are summarized in Table IV.

TABLE IV

| Test No. | Temperature [°C.] | Test time [h] | DMA feed [g] | Amount discharged [g] | Cyclopentanone [mol %] | DMA [mol %] | Conversion [%] | Selectivity [%] |
|---|---|---|---|---|---|---|---|---|
| 1 | 330 | 4.5 | 730 | 758 | 54 | 40 | 60 | 90 |
| 2 | 350 | 3 | 490 | 437 | 77 | 13 | 87 | 89 |
| 3 | 360 | 6.5 | 1079 | 837 | 80 | 2 | 98 | 82 |

EXAMPLE 8

10 ml/hour of a mixture of 79% by weight of dimethyl 1,7-hexanedioate, 13.4% by weight of methanol and 7.6% by weight of water (molar ratio of diester to H$_2$O=1:1) were pumped into an evaporator and fed from there, together with 3 l of nitrogen, over 10 g (15 ml) of catalyst (particle size 0.5 mm). The gaseous reacted mixtures were condensed in cold traps, weighed and analyzed by gas chromatography. The results are shown in Table V.

TABLE V

| No. | Temperature [°C.] | Test time [h] | Diester feed [g] | Amount discharged [g] | Cyclohexanone [mol %] | Diester [mol %] | Conversion [%] | Selectivity [%] | Catalyst |
|---|---|---|---|---|---|---|---|---|---|
| 1 | 340 | 30 | 253 | 270 | 35 | 58 | 42 | 83 | A |
| 2 | 350 | 24 | 188 | 186 | 35 | 54 | 65 | 54 | B |
| 3 | 400 | 24 | 188 | 209 | 70 | 30 | 70 | 100 | C |
| 4 | 370 | 24 | 188 | 220 | 20 | 63 | 37 | 54 | D |

Catalyst A: γ-alumina
Catalyst B: cobalt oxide (20%)/silica gel (80%)
Catalyst C: lithium oxide (13.5%)/magnesium oxide (86.5%)
Catalyst D: cesium oxide (13.5%)/silica gel (86.5%)

EXAMPLE 9

10 ml/hour of a mixture of 71% by weight of dimethyl 1,8-octanedioate, 22.6% by weight of methanol and 6.4% by weight of water (molar ratio of diester to H$_2$O=1:1) were pumped into an evaporator and fed from there, together with 3 l of nitrogen, over 10 g (15 ml) of catalyst (particle size 0.5 mm). The gaseous reacted mixtures were condensed in cold traps, weighed, and analyzed by gas chromatography. The results are summarized in Table VI.

TABLE VI

| No. | Temperature [°C.] | Test time [h] | Diester feed [g] | Amount discharged [g] | Cycloheptanone [mol %] | Diester [mol %] | Conversion [%] | Selectivity [%] | Catalyst |
|---|---|---|---|---|---|---|---|---|---|
| 1 | 340 | 24 | 161 | 208 | 14 | 66 | 34 | 41 | A |
| 2 | 350 | 14 | 94 | 104 | 13 | 67 | 33 | 39 | B |
| 3 | 350 | 20 | 136 | 177 | 27 | 54 | 46 | 59 | C |

Catalyst A: γ-alumina
Catalyst B: cobalt oxide (20%)/silica gel (80%)
Catalyst C: cesium oxide (18.6%)/silica gel (86.5%)

EXAMPLE 10

50 ml/hour of dimethyl 1,7-hexanedioate and 33 ml/hour of water were vaporized at about 300° C. and passed, together with 100 l of nitrogen, over 300 g (380 ml) of fluidized γ-alumina catalyst (particle size 0.14–0.315 mm) at 345° C. The gaseous reacted mixture was condensed in cold traps and analyzed by gas chromatography. The result is shown in Table VII.

TABLE VII

| Test time [h] | Diester feed [g] | Amount discharged [g] | Cyclohexanone [mol %] | Diester [mol %] | Conversion [%] | Selectivity [%] |
|---|---|---|---|---|---|---|
| 6 | 287 | 453 | 85 | 12 | 88 | 96 |

EXAMPLE 11

50 ml/hour of dimethyl 1,8-octanedioate and 33 ml/hour of water were vaporized at about 300° C. and passed, together with 100 l of nitrogen, over 300 g (380 ml) of fluidized γ-alumina catalyst (particle size 0.14–0.315 mm) at 345° C. The gaseous reacted mixture was condensed in cold traps and analyzed by gas chromatography. The result is shown in Table VIII.

TABLE VIII

| Test time [h] | Diester feed [g] | Amount discharged [g] | Cycloheptanone [mol %] | Diester [mol %] | Conversion [%] | Selectivity [%] |
|---|---|---|---|---|---|---|
| 6 | 299 | 487 | 29 | 42 | 58 | 50 |

EXAMPLE 12

750 parts by volume (490 parts by weight) of γ-alumina having a particle size of from 0.06 to 0.2 mm were introduced, as the catalyst, into a fluidized-bed reactor, the lower part of which contained a distributor plate for the reaction gas and the upper part of which possessed a separating apparatus for catalyst dust. The catalyst was fluidized with 75,000 parts by volume of nitrogen and heated to 340° C. 316 parts by weight/hour of DMA and 66 parts by weight/hour of water were vaporized in a stream of nitrogen at 290° C. and passed through the catalyst bed at 340° C. A total of 3,240 parts by weight of DMA were used. Condensation and washing of the exit gas with methanol gave 3,179 parts by weight of crude product, which contained 1,312 parts by weight of cyclopentanone and 51 parts by weight of DMA in addition to water and methanol. The yield was 85.2 mol %, based on converted DMA.

We claim:

1. A process for the preparation of a cyclic ketone of the formula

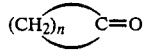

where n is an integer from 4 to 6, wherein an aliphatic dicarboxylate of the formula

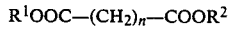

where n has the above meaning and $R^1$ and $R^2$ are each alkyl of 1 to 12 carbon atoms, cycloalkyl of 5 or 6 carbon atoms, aralkyl or aryl and $R^2$ may furthermore be hydrogen, is converted at from 150° to 450° C. over a solid oxide catalyst.

2. A process as claimed in claim 1, wherein the catalyst used is an oxide of an element of main groups I to V or of subgroups I to VIII of the periodic table of elements or an oxide of the rare earth metals.

3. A process as claimed in claim 1, wherein the catalyst used is magnesium oxide, alumina, silica, zinc oxide or titanium dioxide.

4. A process as claimed in claim 1, wherein the catalyst used is magnesium oxide, alumina or silica.

5. A process as claimed in claim 1, wherein the catalyst used is alumina.

6. A process as claimed in claim 1, wherein the conversion of the ester (II) is carried out with the addition of water, a molar ratio II to water of from 1:0.05 to 1:20, in particular from 1:0.1 to 1:5, being chosen.

7. A process as claimed in claim 1, wherein the reaction according to the invention is carried out in a fluidized bed.

8. A process as claimed in claim 1, wherein the reaction is carried out at from 300° to 345° C.

* * * * *